United States Patent [19]

Nagel et al.

[11] Patent Number: 6,020,335
[45] Date of Patent: Feb. 1, 2000

[54] (N-(PYRIDINYLMETHYL)-HETEROCYCLIC) YLIDENEAMINE COMPOUNDS AS NICOTINIC ACETYLCHOLINE RECEPTOR BINDING AGENTS

[75] Inventors: Arthur A. Nagel, Gales Ferry; Steven W. Goldstein, Noank; Stanley Jung, Groton; Peter H. Dorff, Norwich, all of Conn.

[73] Assignee: Pfizer Inc, New York, N.Y.

[21] Appl. No.: 08/963,852

[22] Filed: Nov. 4, 1997

Related U.S. Application Data

[60] Provisional application No. 60/038,036, Feb. 6, 1997.
[51] Int. Cl.$^7$ ............ C07D 213/62; C07D 213/44; C07D 213/79; C07D 213/36
[52] U.S. Cl. .................. 514/253; 514/332; 514/337; 514/340; 544/2; 544/8; 544/238; 546/261; 546/262; 546/263; 546/264; 546/268.4; 546/276.4
[58] Field of Search .................. 546/261, 262, 546/263, 264, 268.4, 276.4; 544/2, 8, 238; 514/253, 332, 337, 340

[56] References Cited

U.S. PATENT DOCUMENTS 5,814,645  9/1998  Kanellakopulos .................. 514/332

*Primary Examiner*—D. Margaret Seaman
*Attorney, Agent, or Firm*—Peter C. Richardson; Paul H. Ginsburg; Israel Nissenbaum

[57] ABSTRACT

An (N-(pyridinylmethyl)-heterocyclic)ylideneamine compound of the formula

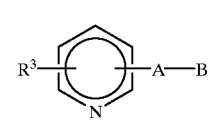

I wherein $R^3$, A, and B are as described below, and its pharmaceutically acceptable salts and prodrugs. Compounds of the formula I and their pharmaceutically acceptable salts and prodrugs are useful in the treatment of addictive disorders, such as the use of tobacco or other nicotine containing products, neurological and mental disorders such as senile dementia of the Alzheimer's type, Parkinson's disease, attentional hyperactivity disorder, anxiety, obesity, Tourette's Syndrome and ulcerative colitis.

16 Claims, No Drawings

(N-(PYRIDINYLMETHYL)-HETEROCYCLIC) YLIDENEAMINE COMPOUNDS AS NICOTINIC ACETYLCHOLINE RECEPTOR BINDING AGENTS

This is a continuation of provisional application 60/038,036 filed Feb 6, 1997, the benefit of which is hereby claimed under 37 C.F.R. §1.78(a)(3).

BACKGROUND OF THE INVENTION

This invention relates to heterocyclic compounds. More particularly it relates to (N-(pyridinylmethyl)-heterocyclic)-2-ylideneamine compounds of the formula I below. Compounds of formula I are useful in the treatment of addictive disorders such as the use of tobacco or other nicotine containing products. These compounds are also useful in the treatment of neurological and mental disorders such as senile dementia of the Alzheimer's type, Parkinson's disease, attentional hyperactivity disorder, anxiety, obesity, Tourette's Syndrome and ulcerative colitis.

Substances which can deliver pharmacologically relevant amounts of nicotine to the central nervous system are among the most abused substances known. These include, but not are not limited to tobacco cigarettes, and "chewing tobacco" (see J. E. Henningfield, Ph.D, *New England Journal of Med.*, 1196,1995). Cigarette smoking has been tied to increased risk for lung cancer, emphysema and heart disease and it is estimated 400,000 people will die in 1995 from the combined effects of nicotine abuse in the United States (see J. A. Califano, Jr., *New England Journal of Med.* 1214, 1995). Nicotine is a highly addicting drug with 40% of those who try smoking later becoming physically dependent upon it. Attempts to quit the use of nicotine, such as in smoking, have been largely ineffective with >80% of such attempts ending in failure. Most attempts to quit end in failure in the first week due to intense withdrawal and craving symptoms. An effective therapy should prevent withdrawal symptoms, relieve craving and, simultaneously, antagonize the reinforcing effects of nicotine obtained through smoking. Currently, few therapies are available for smoking cessation and most involve replacement of cigarettes with nicotine in the form of a patch or gum. A high rate of relapse and low overall success in ending nicotine use is evidence of the need for additional and more effective therapies for treatment of nicotine addiction than the nicotine patch or gum.

Pharmaceutical compositions employed for the treatment of chronic nicotinism and addiction to nicotine can be divided into two groups. The first covers salts of silver, iron and copper. These substances are employed to develop a negative reflex to smoking usually in the form of a solution, or by incorporation in chewing gum compositions. The resultant reflex is based on the appearance of a strong unpleasant taste in the mouth during smoking after a preliminary rinsing of the mouth cavity with solutions of salts, or after the use of a chewing gum containing such salts (See Nasirov et al. *"Anabasine Hydrochloride—New Antismoking Agent"*, *Chemico-Pharmaceutical Journal, vol. XII*, 1978, No. 2, 149–152).

The second group of agents that are used for the suppression of nicotine addiction comprises substances of an alkaloidal nature, such as cytisine, lobeline and anabasine hydrochloride, possessing an effect on H-cholinoreactive systems of the organism similar to that of nicotine. The mechanism of their effect is due to their structural similarity with nicotine and the possible "competitive" antagonism between these alkaloids and nicotine (F. R. Khalikova, S. H. Nasirov, *"On pharmacology of the Alkaloid Anabasine and some Polymeric and Copolymeric Derivatives Thereof"*, in Coll. *"Pharmacology of Vegetable Compounds"*, *Proceedings of Tashkent University*, 457, 1973, 5–16).

U.S. Pat. No. 4,971,079 describes a composition comprising a biologically resorbable polymer containing a cation exchange group modified by an antinicotine action alkaloid, such as anabasine or cytisine, and a gum containing same. However, it has been found that the potency of cytisine is not high due to its inability to penetrate the brain barrier. (Reavill, C. et al., *Behavioural and Pharmacokinetic Studies On Nivotine, Cytisine and Lobeline, Neuropharmacology*, 29, 619–624 (1990)).

Labadie L. C. (in *Peut-on supprimer les facteurs de risque en bronchopatie chronique et en particulier le tabac, Mediater. med.*, 1976, 4, No. 112, 97, 99) describes the use of leaves of other night-shade plants, such as potato, tomato, eggplant and digitalis as tobacco substitutes.

One of the most successful approaches to date in reducing the incidence of smoking relies upon nicotine containing chewing gum which is designed to reduce smoking withdrawal symptoms. The reported success rate, while still relatively low, is approximately twice that of the other methods which have heretofore been employed. (See *British Medical Journal*, 286, (1983)).

The use of the nicotine gum suffers from several problems including bad taste, destruction of dental appliances and gastrointestinal discomfort thereby reducing their use to suppress nicotine addiction. In addition, it has been found that the nicotine containing gum does not completely satisfy the craving that most smokers experience for nicotine and often nicotine gum becomes addictive to the patient.

A simulated smoking device which uses a source of vaporizable nicotine is claimed in U.S. Pat. No. 4,284,089. While the cigarette itself is non-combustible it delivers a nicotine-containing vapor which may not raise the nicotine level in the blood sufficiently to satisfy a smoker. Thus, it has not been shown to satisfy the desire for a certain nicotine level in the blood to which many smokers have become accustomed and, even more so, upon which many smokers have become dependent. In addition, the simulated smoking devices of the type taught in U.S. Pat. No. 4,284,089 also suffer from the bad taste of a substantial amount of nicotine introduced into the oral cavity. More importantly, this nicotine does not penetrate into the chest for stimulating and providing that sensation normally provided by nicotine and to which the smoker has become accustomed.

The current first line therapy for smoking cessation, as described in U.S. Pat. No. 5,016,652 describes a transdermal patch which is useful for the controlled delivery of nicotine to the bloodstream of the user thereby reducing the incidence of smoking. Clinical trials have shown that abstinence rates (with the nicotine patch) of 30 to 40% can be achieved during the first six weeks of application (K. J. Palmer, M. M. Buckley, D. Faulds; Drugs 44(3) 498–529, (1992) compared with 4 to 21% with a placebo. However, long term abstinence rates (>6 months) are considerably lower; falling to between 11–18%. Thus, a more effective therapy which will afford a greater percentage of smokers who are able to quit is clearly needed.

International Patent Publication WO 92/15564 describes compounds of the formula (R)

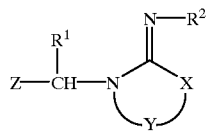

(R)

wherein Z is defined, inter alia, as optionally substituted pyridin-3-yl and X and Y are as defined therein. The compounds of formula (R) wherein $R^2$ is hydrogen are useful as intermediates in the preparation of the compounds of formula (R) wherein $R^2$ is not hydrogen. Compounds of the formula (R) wherein $R^2$ is not H are claimed to be useful as insecticides. There is no teaching, or suggestion, in the reference that compounds of the formula (R) wherein $R^2$ is H or has the other indicated meanings can be used in the treatment of addictive disorders such as the use of tobacco or other nicotine containing products or in the treatment of neurological and mental disorders.

A copending application (Attorney's Docket No. PC9582), assigned to the assignee of this application and incorporated herein in its entirety, refers to pyridine-fuse heterocyclic compounds which are useful in the treatment of addictive disorders such as the use of tobacco or other nicotine containing products or in the treatment of neurological and mental disorders.

Copending application (Attorney's Docket No. PC9728), assigned to the assignee of this application and incorporated herein in its entirety, refers to 7-aza bicycloheptanes which are useful in the treatment of addictive disorders such as the use of tobacco or other nicotine containing products or in the treatment of neurological and mental disorders.

SUMMARY OF THE INVENTION

The present invention relates to (N-(pyridinylmethyl)-heterocyclic)ylideneamines of the formula

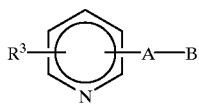

I and or a pharmaceutically acceptable acid addition salt or prodrug thereof, wherein A is —CH(R)— and R is hydrogen or optionally substituted $(C_1-C_6)$alkyl wherein the substituents comprise one or more groups individually selected from hydroxy, $(C_1-C_6)$alkoxy, oxo, $(C_2-C_6)$alkanoyl and $NR^4R^5$; and B is a group of the formula

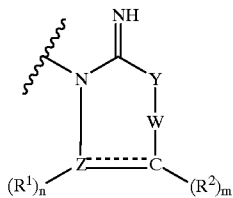

wherein Y-W is $CH_2$, NH, O, S, $CH_2CH_2$, CH=CH, N=CH, NH—$CH_2$, OCH2 or $SCH_2$;

the dotted line represents an optional bond;

Z is C, N, O or S;

m is 1 or 2;

n is 0, 1 or 2 with the proviso that n is 0 when Z is O or S, n is 1 when Z is N and n is 2 when Z is C;

each $R^1$ and $R^2$ is independently selected from hydrogen, optionally substituted $(C_1-C_6)$alkyl, optionally substituted $(C_1-C_6)$alkoxy and optionally substituted $(C_2-C_6)$alkanoyl, wherein the substituents on the alkyl or alkanoyl groups are selected from hydroxy, $(C_1-C_6)$alkoxy, oxo, $(C_2-C_6)$alkanoyl and $NR^4R^5$, or $R^1$ and $R^2$ together with the carbon atoms to which they are attached form an optionally substituted phenyl ring or six membered heteroaromatic ring containing at least one heteroatom selected from N, S and O and Z is C wherein said substituents are selected from optionally substituted $(C_1-C_6)$alkyl or optionally substituted $(C_1-C)$alkoxy wherein said substituents are selected from $(C_1-C_6)$alkyl, optionally substituted $(C_1-C_6)$alkoxy and optionally substituted $(C_2-C_6)$alkanoyl or $R^1$ and one of $R^2$ together form a bond with the proviso that $R^1$ and $R^2$ cannot form a bond when Z is O or S;

$R^3$ is hydrogen or halo; and $R^4$ and $R^5$ are each independently selected from hydrogen and optionally substituted $(C_1-C_6)$alkyl wherein said substituents are selected from $(C_1-C_6)$alkyl and halo;

with the provisos that when -B-A is attached to the 3-position of the pyridine ring and R is hydrogen and a) $R^3$ is 6-chloro and
   i) Z is C, the dotted line represents a bond, m and n are both 1, $R^1$ and $R^2$ are both hydrogen, then W-Y is not selected from CH=CH, S, $CH_2$, NH, CH=N, $OCH_2$ or $SCH_2$;
   ii) Z is nitrogen, the dotted line represents a bond, n is 0 and m is 1 then $R^2$ is not $CF_3$; or
   iii) Z is C, the dotted line represents a bond, m and n are both 2, and each $R^1$ and $R^2$ is hydrogen, then W-Y is not S; or b) $R^3$ is hydrogen, 6-bromo or 6-fluoro and Z is carbon, the dotted line represents a bond, m and n are both 1, $R^1$ and $R^2$ are both hydrogen, then W-Y is not sulfur.

Preferred compounds of the formula I are those wherein Z is N, m is 1 or 2, W-Y is S or CH=CH, $R^3$ is halo or H, $R^2$ is $(C_1-C_6)$alkyl or halo, and the dotted line is a bond.

Other preferred compounds of the formula I are those wherein Z is C, R is $(C_1-C_6)$alkyl or hydrogen, m is 1, W-Y is S or CH=CH, the dotted line is a bond, $R^1$ and $R^2$ are each hydrogen or $(C_1-C_6)$alkyl, or the portion of B corresponding to

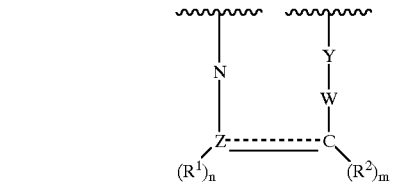

IV is selected from

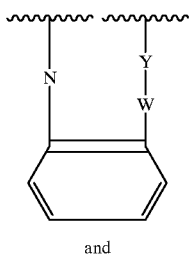

V and

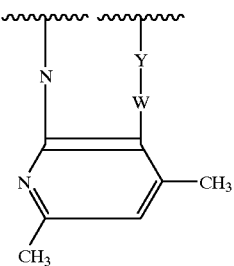

VI

Most preferred compounds of the formula I are selected from the group comprising 3-(6chloro-pyridin-3-ylmethyl)-3H-[1,3,4]thiadiazol-2-ylideneamine;

5-methyl-3-pyridin-3-ylmethyl-3H-thiazol-2-ylideneamine;

3-(6-chloro-pyridin-3-ylmethyl)-5-methyl-3H-[1,3,4]thiadiozol-2-ylideneamine;

6-chloro-2-(6-chloro-pyridin-3-ylmethyl)-2H-pyridazin-3-ylideneamine;

3-(6-chloro-pyridin-3-ylmethyl)-3H-benzothiazol-2-ylideneamine;

3-pyridin-3-ylmethyl-3H-[1,3,4]thiadiazol-2-ylideneamine;

3-[1-(6-chloro-pyridin-3-yl)-ethyl]-3H-thiazol-2-ylideneamine;

3-[1-(6-chloro-pyridin-3-yl)-ethyl]-3H-[1,3,4]thiadiazol-2-ylideneamine;

3-[1-(6-chloro-pyridin-3-ylmethyl)-thiazolidin-2-ylideneamine;

3-pyridin-3-ylmethyl-thiazolidin-2-ylideneamine;

5,7-dimethyl-1-pyridin-3-ylmethyl-3H-[1,8]naphthyridin-2-ylidene;

6-chloro-2-pyridin-3-ylmethyl-2H-pyridazin-3-ylideneamine; and 5-methyl-3-pyridin-3-ylmethyl-3H-[1,3,4]thiadiazol-2-ylideneamine.

Unless otherwise indicated, the term "halo", as used herein, includes fluoro, chloro, bromo and iodo.

Unless otherwise indicated, the term "alkyl", as used herein, may be straight, branched or cyclic, and may include straight and cyclic moieties as well as branched and cyclic moieties.

The compounds of formula I may have optical centers and therefore may occur in different stereoisomeric configurations. The invention includes all stereolsomers of such compounds of formula I, including mixtures thereof.

The present invention also relates to all radiolabelled forms of the compounds of formula I comprising at least one radiolabel preferably selected from $^3H, ^{11}C$ and $^{14}C$. Such radiolabelled compounds are useful as research and diagnostic tools in metabolism pharmacokinetic studies and in binding assays in both animals and man.

In addition, the present invention relates to pharmaceutical composition for use in reducing nicotine addiction in a mammal comprising an amount of a compound of the formula I, above, or a pharmaceutically acceptable salt or prodrug thereof, effective in reducing nicotine addiction and a pharmaceutically acceptable carrier, wherein A is —CH(R)— and R is hydrogen or optionally substituted ($C_1$–$C_6$) alkyl wherein the substituents comprise one or more groups individually selected from hydroxy, ($C_1$–$C_6$)alkoxy, oxo, ($C_2$–$C_6$)alkanoyl and $NR^4R^5$; and B is a group of the formula

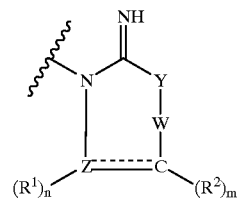

wherein Y-W is $CH_2$, NH, O, S, $CH_2CH_2$, CH=CH, N=CH, NH—$CH_2$, $OCH_2$ or $SCH_2$;

the dotted line represents an optional bond;

Z is C, N, O or S;

m is 1 or 2;

n is 0, 1 or 2 with the proviso that n is 0 when Z is O or S, n is 1 when Z is N and n is 2 when Z is C;

each $R^1$ and $R^2$ is independently selected from hydrogen, optionally substituted ($C_1$–$C_6$)alkyl, optionally substituted ($C_1$–$C_{r6}$)alkoxy and optionally substituted ($C_2$–$C_{,6}$)alkanoyl, wherein the substituents on the alkyl or alkanoyl groups are selected from hydroxy, ($C_1$–$C_6$) alkoxy, oxo, ($C_2$–$C_6$)alkanoyl and $NR^4R^5$, or $R^1$ and $R^2$ together with the carbon atoms to which they are attached form an optionally substituted phenyl ring or six membered heteroaromatic ring containing at least one heteroatom selected from N, S and O and Z is C wherein said substituents are selected from optionally substituted ($C_1$–$C_6$)alkyl or optionally substituted ($C_1$–$C_6$)alkoxy wherein said substituents are selected from ($C_1$–$C_6$)alkyl, optionally substituted ($C_1$–$C_6$) alkoxy and optionally substituted ($C_2$–$C_6$)alkanoyl or $R^1$ and one of $R^2$ together form a bond with the proviso that $R^1$ and $R^2$ cannot form a bond when Z is O or S;

$R^3$ is hydrogen or halo; and $R^4$ and $R^5$ are each independently selected from hydrogen and optionally substituted ($C_1$–$C_6$)alkyl wherein said substituents are selected from ($C_1$–$C_6$)alkyl and halo.

The present invention relates to a composition, as described above, wherein the compound of the formula I is selected from the group consisting of 3-(6-chloro-pyridin-3-ylmethyl)-3H-[1,3,4]thiadiazol-2-ylideneamine;

3-pyridin-3-ylmethyl-3H-thiazol-2-ylideneamine;

3-(6-chloro-pyridin-3-ylmethyl)-3H-thiazol-2-ylideneamine;

3-(6-chloro-pyridin-3-ylmethyl)-4-methyl-3H-thiazol-2-ylideneamine;

3-(6-chloro-pyridin-3-ylmethyl)-methyl-3H-thiazol-2-ylideneamine;

5-methyl-3-pyridin-3-ylmethyl-3H-thiazol-2-ylideneamine;

3-(6-chloro-pyridin-3-ylmethyl)-5methyl-3H-[1,3,4]thiadiozol-2-ylideneamine;

6-chloro-2-(6-chloro-pyridin-3-ylmethyl)-2H-pyridazin-3-ylideneamine;

3-(6-chloro-pyridin-3-ylmethyl)-3H-benzothiazol-2-ylideneamine;

3-pyridin-3-ylmethyl-3H-[1,3,4]thiadiazol-2-ylideneamine;

3-[1-(6-chloro-pyridin-3-yl)-ethyl]-3H-thiazol-2-ylideneamine;

3-[1-(6-chloro-pyridin-3-yl)-ethyl]-3H-[1,3,4]thiadiazol-2-ylideneamine;

3-[1-(6-chloro-pyridin-3-ylmethyl)-thiazolidin-2-ylideneamine;

3-pyridin-3-ylmethyl-thiazolidin-2-ylideneamine;

5,7-dimethyl-1-pyridin-3-ylmethyl-3H-[1,8]naphthyridin-2-ylidene;

6-chloro-2-pyridin-3-ylmethyl-2H-pyridazin-3-ylideneamine; and 5-methyl-3-pyridin-3-ylmethyl-3H-[1,3,4]thiadiazol-2-ylideneamine.

In another embodiment the present invention relates to a method for reducing nicotine addiction in a mammal, comprising administering to said mammal an amount of a compound of the formula I, or a pharmaceutically acceptable salt or prodrug thereof, effective in reducing nicotine addiction wherein A is —CH(R)— and R is hydrogen or optionally substituted ($C_1$–$C_6$)alkyl wherein the substituents comprise one or more groups individually selected from hydroxy, ($C_1$–$C_6$)alkoxy, oxo, ($C_2$–$C_6$)alkanoyl and $NR^4R^5$; and B is a group of the formula

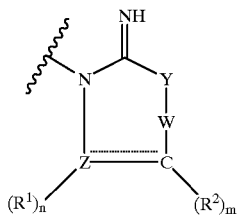

wherein Y-W is $CH_2$, NH, O, S, $CH_2CH_2$, CH=CH, N=CH, NH—$CH_2$, $OCH_2$ or $SCH_2$;

the dotted line represents an optional bond;

Z is C, N, O or S;

m is 1 or 2;

n is 0, 1 or 2 with the proviso that n is 0 when Z is O or S, n is 1 when Z is N and n is 2 when Z is C;

each $R^1$ and $R^2$ is independently selected from hydrogen, optionally substituted ($C_1$–$C_6$)alkyl, optionally substituted ($C_1$–$C_6$)alkoxy and optionally substituted ($C_2$–$C_6$)alkanoyl, wherein the substituents on the alkyl or alkanoyl groups are selected from hydroxy, ($C_1$–$C_6$) alkoxy, oxo, ($C_2$–$C_6$)alkanoyl and $NR^4R^5$, or $R^1$ and $R^2$ together with the carbon atoms to which they are attached form an optionally substituted six membered heteroaromatic ring containing at least one heteroatom selected from N, S and O and Z is C wherein said substituents are selected from optionally substituted ($C_1$–$C_6$)alkyl or optionally substituted ($C_1$–$C_6$)alkoxy wherein said substituents are selected from ($C_1$–$C_6$) alkyl, optionally substituted ($C_1$–$C_6$)alkoxy and optionally substituted ($C_2$–$C_6$)alkanoyl or $R^1$ and one of $R^2$ together form a bond with the proviso that $R^1$ and $R^2$ cannot form a bond when Z is O or S;

$R^3$ is hydrogen or halo; and $R^4$ and $R^5$ are each independently selected from hydrogen and optionally substituted ($C_1$–$C_6$)alkyl wherein said substituents are selected from ($C_1$–$C_6$)alkyl and halo.

In another aspect of the above embodiment the compound of the formula I is selected from the group consisting of 3-(6-chloro-pyridin-3-ylmethyl)-3H-[1,3,4]thiadiazol-2-ylideneamine;

3-pyridin-3-ylmethyl-3H-thiazol-2-ylideneamine;

3-(6-chloro-pyridin-3-ylmethyl)-3H-thiazol-2-ylideneamine;

3-(6-chloro-pyridin-3-ylmethyl)-4-methyl-3H-thiazol-2-ylideneamine;

3-(6-chloro-pyridin-3ylmethyl)-4-methyl-3H-thiazol-2-ylideneamine;

5-methyl-3-pyridin-3-ylmethyl-3H-thiazol-2-ylideneamine;

3-(6-chloro-pyridin-3ylmethyl)-5-methyl-3H-[1,3,4]thiadiozol-2-ylideneamine;

6-chloro-2-(6-chloro-pyridin-3-ylmethyl)-2H-pyridazin-3-ylideneamine;

3-(6-chloro-pyridin-3-ylmethyl)-3H-benzothiazol-2-ylideneamine;

3-pyridin-3-ylmethyl-3H-[1,3,4]thiadiazol-2-ylideneamine;

3-[1-(6chloro-pyridin-3yl)-ethyl]-3H-thiazol-2-ylideneamine;

3-[1-(6-chloro-pyridin-3-yl)-ethyl]-3H-[1,3,4]thiadiazol-2-ylideneamine;

3-[1-(6-chloro-pyridin-3-ylmethyl)-thiazolidin-2-ylideneamine;

3-pyridin-3-ylmethyl-thiazolidin-2-ylideneamine;

5,7-dimethyl-1-pyridin-3-ylmethyl-3H -[1,8]naphthyridin-2-ylidene;

6-chloro-2-pyridin-3ylmethyl-2H-pyridazin-3-ylideneamine; and 5-methyl-3pyridin-3-ylmethyl-3H-[1,3,4]thiadiazol-2-ylideneamine.

Yet another aspect of the present invention relates to compounds of formula I wherein said pharmaceutically acceptable acid addition salts are the salts of acids selected from the group comprising hydrochloric acid, p-toluenesulfonic acid, fumaric acid, citric acid, succinic acid, salicyclic acid, oxalic acid, hydrobromic acid, phosphoric acid, methanesulfonic acid, tartaric acid, di-p-toluoyl tartaric acid, and mandelic acid.

Another embodiment of present invention relates to a method for treating nicotine addiction or neurological or mental disorders in a mammal which comprises administering to said mammal an amount of a compound of the formula I effective in treating nicotine addiction or neurological or mental disorders wherein A is —CH(R)— and R is hydrogen or optionally substituted ($C_1$–$C_6$)alkyl wherein the substituents comprise one or more groups individually selected from hydroxy, ($C_1$–$C_6$)alkoxy, oxo, ($C_2$–$C_6$) alkanoyl and $NR^4R^5$; and B is a group of the formula

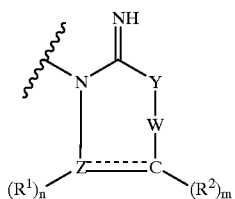

wherein Y-W is $CH_2$, NH, O, S, $CH_2CH_2$, CH=CH, N=CH, NH—$CH_2$, $OCH_2$ or $SCH_2$;

the dotted line represents an optional bond;

Z is C, N, O or S;

m is 1 or 2;

n is 0, 1 or 2 with the proviso that n is 0 when Z is O or S, n is 1 when Z is N and n is 2 when Z is C;

each $R^1$ and $R^2$ is independently selected from hydrogen, optionally substituted ($C_1$–$C_6$)alkyl, optionally substituted ($C_1$–$C_6$)alkoxy and optionally substituted ($C_2$–$C_6$)alkanoyl, wherein the substituents on the alkyl or alkanoyl groups are selected from hydroxy, ($C_1$–$C_6$) alkoxy, oxo, ($C_2$–$C_6$)alkanoyl and $NR^4R^5$, or $R^1$ and $R^2$ together with the carbon atoms to which they are attached form an optionally substituted six membered heteroaromatic ring containing at least one heteroatom selected from N, S and O and Z is C wherein said substituents are selected from optionally substituted ($C_1$–$C_6$)alkyl or optionally substituted ($C_1$–$C_6$)alkoxy wherein said substituents are selected from ($C_1$–$C_6$) alkyl, optionally substituted ($C_1$–$C_6$)alkoxy and optionally substituted ($C_2$–$C_6$)alkanoyl or $R^1$ and one of $R^2$ together form a bond with the proviso that $R^1$ and $R^2$ cannot form a bond when Z is O or S;

$R^3$ is hydrogen or halo; and $R^4$ and $R^5$ are each independently selected from hydrogen and optionally substituted ($C_1$–$C_6$)alkyl wherein said substituents are selected from ($C_1$–$C_6$)alkyl and halo.

According to another aspect of the embodiment the compound of the formula I is selected from selected from the group consisting of 3-(6-chloro-pyridin-3-ylmethyl)-3H-[1,3,4]thiadiazol-2-ylideneamine;

3-pyridin-3-ylmethyl-3H-thiazol-2-ylideneamine;

3-(6-chloro-pyridin-3-ylmethyl)-3H-thiazol-2-ylideneamine;

3-(6-chloro-pyridin-3-ylmethyl)-4methyl-3H-thiazol-2-ylideneamine;

3-(6-chloro-pyridin-3-ylmethyl)-4methyl-3H-thiazol-2-ylideneamine;

5-methyl-3-pyridin-3-ylmethyl-3H-thiazol-2-ylideneamine;

3-(6-chloro-pyridin-3-ylmethyl)-5-methyl-3H-[1,3,4]thiadiozol-2-ylideneamine;

6-chloro-2-(6-chloro-pyridin-3-ylmethyl)-2H-pyridazin-3-ylideneamine;

3-(6-chloro-pyridin-3-ylmethyl)-3H-benzothiazol-2-ylideneamine;

3-pyridin-3-ylmethyl-3H-[1,3,4]thiadiazol-2-ylideneamine;

3-[1-(6-chloro-pyridin-3-yl)-ethyl]-3H-thiazol-2-ylideneamine;

3-[1-(6-chloro-pyridin-3-yl)-ethyl]-3H-[1,3,4]thiadiazol-2-ylideneamine;

3-[1-(6-chloro-pyridin-3-ylmethyl)-thiazolidin-2-ylideneamine;

3-pyridin-3-ylmethyl-thiazolidin-2-ylideneamine;

5,7-dimethyl-1-pyridin-3-ylmethyl-3H-[1,8]naphthyridin-2-ylidene;

6-chloro-2-pyridin-3-ylmethyl-2H-pyridazin-3-ylideneamine; and 5-methyl-3-pyridin-3-ylmethyl-3H-[1,3,4]thiadiazol-2-ylideneamine.

Yet another embodiment of present invention relates to a composition for treating nicotine addiction or and neurological or mental disorders in a mammal comprising an amount of a compound of the formula I effective in treating nicotine addiction or and neurological or mental disorders wherein A is —CH(R)— and R is hydrogen or optionally substituted ($C_1$–$C_6$)alkyl wherein the substituents comprise one or more groups individually selected from hydroxy, ($C_1$–$C_6$)alkoxy, oxo, ($C_2$–$C_6$)alkanoyl and $NR^4R^5$; and B is a group of the formula

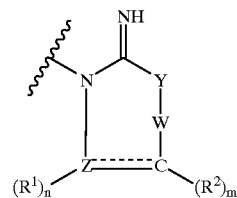

wherein Y-W is $CH_2$, NH, O, S, $CH_2CH_2$, CH=CH, N=CH, NH—$CH_2$, $OCH_2$ or $SCH_2$;

the dotted line represents an optional bond;

Z is C, N, O or S;

m is 1 or 2;

n is 0, 1 or 2 with the proviso that n is 0 when Z is O or S, n is 1 when Z is N and n is 2 when Z is C;

each $R^1$ and $R^2$ is independently selected from hydrogen, optionally substituted ($C_1$–$C_6$)alkyl, optionally substituted ($C_1$–$C_6$)alkoxy and optionally substituted ($C_2$–$C_6$)alkanoyl, wherein the substituents on the alkyl or alkanoyl groups are selected from hydroxy, ($C_1$–$C_6$) alkoxy, oxo, ($C_2$–$C_6$)alkanoyl and $NR^4R^5$, or $R^1$ and $R^2$ together with the carbon atoms to which they are attached form an optionally substituted six membered heteroaromatic ring containing at least one heteroatom selected from N, S and O and Z is C wherein said substituents are selected from optionally substituted ($C_1$–$C_6$)alkyl or optionally substituted ($C_1$–$C_6$)alkoxy wherein said substituents are selected from ($C_1$–$C_6$) alkyl, optionally substituted ($C_1$–$C_6$)alkoxy and optionally substituted ($C_2$–$C_6$)alkanoyl or $R^1$ and one of $R^2$ together form a bond with the proviso that $R^1$ and $R^2$ cannot form a bond when Z is O or S;

$R^3$ is hydrogen or halo; and $R^4$ and $R^5$ are each independently selected from hydrogen and optionally substituted ($C_1$–$C_6$)alkyl wherein said substituents are selected from ($C_1$–$C_6$)alkyl and halo.

According to another aspect of the above embodiment the compound of the formula I is selected from the group consisting of 3-(6-chloro-pyridin-3-ylmethyl)-3H-[1,3,4]thiadiazol-2-ylideneamine;

3-pyridin-3-ylmethyl-3H-thiazol-2-ylideneamine;

3-(6-chloro-pyridin-3-ylmethyl)-3H-thiazol-2-ylideneamine;

3-(6-chloro-pyridin-3-ylmethyl)-4-methyl-3H-thiazol-2-ylideneamine;

3-(6-chloro-pyridin-3-ylmethyl)-4-methyl-3H-thiazol-2-ylideneamine;

5-methyl-3-pyridin-3-ylmethyl-3H-thiazol-2-ylideneamine;

3-(6-chloro-pyridin-3-ylmethyl)-5-methyl-3H-[1,3,4]thiadiozol-2-ylideneamine;

6-chloro-2-(6-chloro-pyridin-3-ylmethyl)-2H-pyridazin-3-ylideneamine;

3-(6-chloro-pyridin-3-ylmethyl)-3H-benzothiazol-2-ylideneamine;

3-pyridin-3-ylmethyl-3H-[1,3,4]thiadiazol-2-ylideneamine;

3-[1-(6-chloro-pyridin-3-yl)-ethyl]-3H-thiazol-2-ylideneamine;

3-[1-(6-chloro-pyridin-3-yl)-ethyl]-3H-[1,3,4]thiadiazol-2-ylideneamine;

3-[1-(6-chloro-pyridin-3-ylmethyl)-thiazolidin-2-ylideneamine;

3-pyridin-3-ylmethyl-thiazolidin-2-ylideneamine;

5,7-dimethyl-1-pyridin-3-ylmethyl-3H-[1,8]naphthyridin-2-ylidene;

6-chloro-2-pyridin-3-ylmethyl-2H-pyridazin-3-ylideneamine; and 5-methyl-3-pyridin-ylmethyl-3H-[1,3,4]thiadiazol-2-ylideneamine.

Examples of pharmaceutically acceptable acid addition salts of the compounds of formula I are the salts of hydrochloric acid, p-toluenesulfonic acid, fumaric acid, citric acid, succinic acid, salicyclic acid, oxalic acid, hydrobromic acid, phosphoric acid, methanesulfonic acid, tartaric acid, di-p-toluoyl tartaric acid, and mandelic acid.

DETAILED DESCRIPTION OF THE INVENTION

In the following Schemes and discussion R, $R^1$, $R^2$, $R^3$, $R^4$, $R^5$, A, B, X, W-Y, Z. m, and n have the meanings given above.

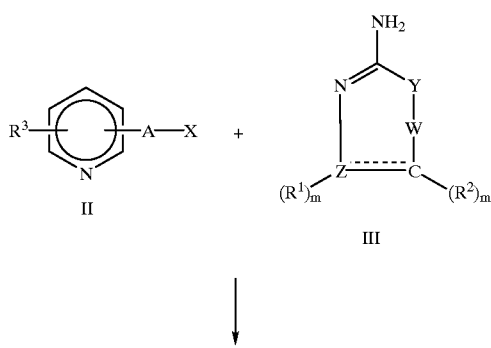

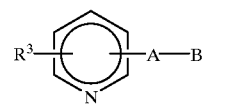

I   ($R^3$ = halo)

↓ dehalogenation

I   ($R^3$ = hydrogen)

In each of the reactions discussed below, or illustrated in the Scheme, above, pressure is not critical unless otherwise indicated. Pressures from about 0.5 atmospheres to about 5 atmospheres are generally acceptable with ambient pressure, i.e., about 1 atmosphere, being preferred as a matter of convenience.

As shown in the Scheme compound I is prepared by reacting compound II, wherein X is a leaving group which can be displaced by an amino group, with the compound of the formula III. Leaving groups are well known in the art and include mesylate, tosylate, triflate, acetate and halo. The preferred leaving group is halo. The reaction is usually carried out in an inert solvent such as a ketone, e.g., acetone, or a ($C_1$–$C_6$)alcohol, such as ethanol, in the optional presence of an added base, at a temperature from about room temperature to the reflux temperature of the solvent or mixture of solvents in the presence of a base. The reaction is preferably effected in acetone or ethanol at the reflux temperature of the solvent. Bases that are useful in the above reaction include excess amounts of either of the reactants, the products or are selected from alkali metal carbonates, bicarbarbonates and hydroxides, and organic amines such as TEA, and the like. Generally, the reaction is run in the absence of added bases.

If X, in compound II, is not iodine then the reaction may also be effected in the presence of catalytic or molar excess (relative to the pyridylmethylchloro group) amounts of iodide ions. The iodide ions may be provided in the form of alkali metal iodides, such as NaI and KI, and in the form of organic base hydroiodides such as triethylamine hydroidide. Although the iodide ions are not essential to effect the reaction it is believed that they affect the reaction, for specific reactants, by converting the alkyl chlorides to their corresponding iodides which are more easily aminated. I.e., the rate of amination is usually increased by the presence of iodide ions and rate is proportional to the iodide ion concentration. Preferably, the iodide ions are used in excess amounts.

Compounds of formula II are commercially available or can be prepared by methods known in the art. (See, e.g., J. Het. Chem., 1979, 16, 333–36.)

Compounds of formula III are commercially available.

Compounds of formula I, wherein $R^3$ is a halogen atom, can be dehalogenated to form compounds of formula I wherein $R^3$ is hydrogen by treatment with hydrogen in the presence of a hydrogenation catalyst such as Pd on carbon, Pd(OH)$_2$, Pd/C and Raney Nickel, and the like. The reaction is generally effected in an inert solvent, such as a ($C_1$–$C_6$) alcohol, e.g., methanol, at a $H_2$ pressure from about atmospheric to about 345 kPa (50 psi) at a temperature from about room temperature to the reflux temperature of the solvent. Preferably, the reaction is effected in methanol, at room temperature, using Pd/C and a $H_2$ pressure of about 345 kPa (50 psi) Alternatively, dehalogenation may be effected by treatment with a reducing agent such as $LiAlH_4$ and $(n\text{-butyl})_3SnH$, and mixtures of $LiAlH_4$ and $AlCl_3$. Preferably the dehalogenation is effected by treatment with hydrogen in the presence of a hydrogenation catalyst.

The salts of the compound of formula I are prepared by treating the free base forms thereof with appropriate acids under the general conditions known to the art. For instance, they may be prepared by contacting the the compound (group) of the formula I with an appropriate acid, usually in a stoichiometric ratio, in an aqueous, nonaqueous or partially aqueous medium as appropriate. The salts are recovered by filtratation, by precipitation with a nonsolvent followed by filtration, by evaporation of the solvent, as appropriate, or, in the case of aqueous solutions, by lyophilization. Typical salts which may be prepared are those of hydrochloric acid, p-toluenesulfonic acid, fumaric acid, citric acid, succinic acid, salicyclic acid, oxalic acid, hydrobromic acid, phosphoric acid, methanesulfonic acid, tartaric acid, di-p-toluoyl tartaric acid, and mandelic acid.

The compounds of the formula I and their pharmaceutically acceptable salts (hereafter "the active compounds") can be administered via either the oral, transdermal (e.g., through the use of a patch), intranasal, sublingual, rectal, parenteral or topical routes. Transdermal and oral administration are preferred. These compounds are, most desirably, administered in dosages ranging from about 0.25 mg up to about 1500 mg per day, preferably from about 0.25 to about 300 mg per day in single or divided doses, although variations will necessarily occur depending upon the weight and condition of the subject being treated and the particular route of administration chosen. However, a dosage level that is in the range of about 0.02 mg to about 10 mg per kg of body weight per day is most desirably employed. Variations may nevertheless occur depending upon the weight and condition of the persons being treated and their individual responses to said medicament, as well as on the type of pharmaceutical formulation chosen and the time period and interval during which such administration is carried out. In some instances, dosage levels below the lower limit of the aforesaid range may be more than adequate, while in other case still larger doses may be employed without causing any harmful side effects, provided that such larger doses are first divided into several small doses for administration throughout the day.

The active compounds can be administered alone or in combination with pharmaceutically acceptable carriers or diluents by any of the several routes previously indicated. More particularly, the active compounds can be administered in a wide variety of different dosage forms, e.g., they may be combined with various pharmaceutically acceptable inert carriers in the form of tablets, capsules, transdermal patches, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents. In addition, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (preferably corn, potato or tapioca starch), alginic acid and certain complex silicates, together with granulation binders like polyvinylpyrrolidone, sucrose, gelatin and acacia.

Additionally, lubricating agents such as magnesium stearate, sodium lauryl sulfate and talc can be used for tabletting purposes. Solid compositions of a similar type may also be employed as fillers in gelatin capsules; preferred materials in this connection also include lactose or milk sugar] as well as high molecular weight polyethylene glycols. When aqueous suspensions and/or elixirs are desired for oral administration the active ingredient may be combined with various sweetening or flavoring agents, coloring matter and, if so desired, emulsifying and/or suspending agents, together with such diluents as water, ethanol, propylene glycol, glycerin and various combinations thereof.

For parenteral administration, a solution of an active compound in either sesame or peanut oil or in aqueous propylene glycol can be employed. The aqueous solutions should be suitably buffered, if necessary, and the liquid diluent first rendered isotonic. These aqueous solutions are suitable for Intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

It is also possible to administer the active compounds topically when treating inflammatory conditions of the skin and this can be done by way of creams, jellies, gels, pastes, ointments and the like, in accordance with standard pharmaceutical practice Biological Assay The effectiveness of the active compounds in suppressing nictone binding to specific receptor sites is determined by the following procedure which is a modification of the methods of Lippiello, P. M. and Femandes, K. G. (in *The Binding of L-[$^3H$]Nicotine To A Single Class of High-Affinity Sites in Rat Brain Membranes, Molecular Pharm.*, 29, 448–54, (1986)) and Anderson, D. J. and Americ, S. P. (in *Nicotinic Receptor Binding of $^3H$-Cystisine, $^3H$-Nicotine and $^3H$-Methylcarmbamylcholine In Rat Brain, European J. Pharm.*, 253, 261–67 (1994)).

Procedure

Male Sprague-Dawley rats (200–300 g) from Charles River were housed in groups in hanging stainless steel wire cages and were maintained on a 12 hour light/dark cycle (7 a.m.–7 p.m. light period). They received standard Purina Rat Chow and water ad libitum.

The rats were killed by decapitation. Brains were removed immediately following decapitation. Membranes were prepared from brain tissue according to the methods of Lippiello and Fernandez (*Molec Pharmacol*, 29, 448–454, (1986) with some modifications. Whole brains were removed, rinsed with ice-cold buffer, and homogenized at 0° in 10 volumes of buffer (w/v) using a Brinkmann Polytron™, setting 6, for 30 seconds. The buffer consisted of 50 mM Tris HCl and had a pH of 7.5 at room temperature. The homogenate was sedimented by centrifugation (10 minutes; 50,000×g; 0 to 4° C. The supernatant was poured off and the membranes were gently resuspended with the Polytron and centrifuged again (10 minutes; 50,000×g; 0 to 4° C. After the second centrifugation, the membranes were resuspended in assay buffer at a concentration of 1.0 g/100 mL. The composition of the standard assay buffer was 50 mM Tris HCl, 120 mM NaCl, 5 mM KCl, 2 mM $MgCl_2$, 2 mM $CaCl_2$ and has a pH of 7.4 at room temperature.

Routine assays were performed in borosilicate glass test tubes. The assay mixture typically consisted of 0.9 mg of membrane protein in a final incubation volume of 1.0 mL. Three sets of tubes were prepared wherein the tubes in each set contained 50 μL of vehicle, blank, or test compound solution, respectively. To each tube was added 200 μL of [$^3$H]-nicotine in assay buffer followed by 750 μL of the membrane suspension. The final concentration of nicotine in each tube was 0.9 nM. The final concentration of cytisine in the blank was 1 μM. The vehicle consisted of deionized water containing 30 μL of 1 N acetic acid per 50 mL of water. The test compounds and cytisine were each dissolved in vehicle. Assays were initiated by vortexing after addition of the membrane suspension to the tube. The samples were incubated at 0 to 4° C. in an iced shaking water bath. Incubations were terminated by rapid filtration under vacuum through Whatman GF/B™ glass fiber filters using a Brandel™ multi-manifold tissue harvester. Following the initial filtration of the assay mixture, filters were washed two times with ice-cold assay buffer (5 m each). The filters were then placed in counting vials and mixed vigorously with 20 ml of Ready Safe™ (Beckman) before quantification of radioactivity. Samples were counted in a LKB Wallach Rackbeta™ liquid scintillation counter at 40–50% efficiency. All determinations were in triplicate.

Calculations

Specific binding IX to the membrane is the difference between total binding in the samples containing vehicle only and membrane VII and non-specific binding in the samples containing the membrane and cytisine VIII, i.e., Specific binding=IX=VII–VIII.

Specific binding in the presence of the test compound XI is the difference between the total binding in the presence of the test compound X and non-specific binding VIII, i.e., XI=X–VIII.

% Inhibition=(1-(XI/IX) times 100.

The compounds of the invention, which were tested, exhibited IC$_{50}$ values of less than 2μM.

EXAMPLE 1

N-(6-Chloro-pyridin-3-ylmethyl)-3H-[1,3,4]thiadiazol-2-ylideneamine

A. N-Chloromethyl-6-chloropyridine (717 mg (4.43 mM)) (prepared according to the method of *J. Het. Chem.*, 1979, 16, 333–336), 537 mg (5.31 mM) of 2-amino-1,3,4-thiadiazole and 1.99 g (13.29 mM) of sodium iodide were mixed together in 60 mL of acetone and refluxed for 18 hours. The reaction mixture was cooled to room temperature and the solvent was evaporated. The residue was dissolved in a 1:1 mixture of 50 mL of 10% NaOH and 50 mL of methylene chloride. The organic layer was dried (Na$_2$SO$_4$) and the solvent was evaporated. The residue was chromatographed on silica using 2% methanol in methylene chloride as the eluant. Appropriate fractions were combined to yield 282 mg (28%) of the title product as an oil. $^1$H-NMR (CDCl$_3$) δ 8.45, (d, 1H, J=2.8 Hz), 7.70 (dd, 1H, J=2.8, 10.7 Hz), 7.60 (s, 1H, J=10.7 Hz), 7.28 (d, 1H, J=10.7 Hz), 5.10 (s, 2H).

B. The oil from part A was dissolved in ethyl acetate and treated with HCl gas. A solid precipitate was formed. The solvent was evaporated and the residue dried under high vacuum to yield 256 mg of the hydrochloride salt of the title product as a white amorphous solid. $^{13}$C-NMR (DMSO-d$_6$) δ 167.1, 150.3, 149.9, 145.8, 140.1, 129.5, 124.5, 49.9. Mass spectrum: m/e=227,229.

EXAMPLES 2–13

The title compounds of Examples 2–13 were prepared according to the method of Example 1A.

EXAMPLE 2

N-(Pyridin-3-ylmethyl)-3H-thiazol-2-ylideneamine $^1$H-NMR (CDCl$_3$) δ 8.5 (m, 2H), 7.6 (m, 1H), 7.2 (m, 1H), 6.4 (d, 1H, J=8.5 Hz), 5.2 (d, 1H, J=8.5 Hz), 4.90 (s, 1H). $^{13}$C-NMR (CDCl$_3$) δ 164.4, 149.2, 149.0, 135.5, 132.3, 126.6, 123.7, 98.7, 46.5. Mass spectrum: m/e=192 (p+1).

EXAMPLE 3

N-(6-Chloro-pyridin-3-ylmethyl)-4-methyl-3H-thiazol-2ylideneamine $^1$H-NMR (CDCl$_3$) δ 8.22 (d, 1H, J=4 Hz), 7.56 (dd, 1H, J=4, 8.2 Hz), 7.22 (d, 1H, J=8.2 Hz), 5.42 (s, 1H), 4.88 (s, 2H), 1.80 (s, 3H). $^{13}$C-NMR (CDCl$_3$) δ 165.7, 150.5, 148.1, 137.7, 134.2, 131.8, 124.4, 93.6, 43.3, 14.9. Mass spectrum: m/e=240, 242.

EXAMPLE 4

N-(6-Chloro-pyridin-3-ylmethyl)-4-methyl-3H-thiazol-2-ylideneamine $^1$H-NMR (CDCl$_3$) δ 8.18 (d, 1H, J=4 Hz), 7.55 (dd, 1H, J=4, 8.2 Hz), 7.15 (d, 1H, J=8.2 Hz), 6.20 (br s, 1H). 6.0 (s, 1H), 4.72 (s, 3H), 1.82 (s, 3H). $^{13}$C-NMR (CDCl$_3$) δ 164.6, 150.6, 148.8, 138.5, 131.7, 124.3, 121.9, 111.5, 45.4, 13.1. Mass spectrum: m/e=240, 242.

EXAMPLE 5

5-Methyl-N-(pyridin-3-ylmethyl)-3H-thiazol-2-ylideneamine $^1$H-NMR (CDCl$_3$) δ 8.52 (m, 2H), 7.69 (m, 1H), 7.25 (m, 1H), 6.16 (s, 1H), 5.05 (d, 2H), 2.0 (s, 3H). $^{13}$C-NMR (CDCl$_3$) δ 6166.0, 149.4, 149.0, 135.8, 131.5, 123.8, 122.7, 47.3, 12.9. Mass spectrum: m/e=206 (p+1).

EXAMPLE 6

N-(6-Chloro-pyridin-3-ylmethyl)-5methyl-3H-[1,3,4]thiadiozol-2-ylideneamine $^1$H-NMR (CDCl$_3$) δ 8.28 (d, 1H, J=4 Hz), 7.55 (dd, 1H, J=4, 8.2 Hz), 7.16 (d, 1H, J=8.2 Hz), 6.25 (br s, 1H), 4.92 (s, 2H), 2.12 (s, 3H). $^{13}$C-NMR (CDCl$_3$) δ 162.8, 150.6, 149.4, 148.1, 144.3, 138.9, 137.5, 131.4, 124.1, 123.9, 47.2, 17.0. Mass spectrum: m/e=241, 243.

EXAMPLE 7

6-Chloro-N-(6-chloro-pyridin-3-ylmethyl)-2H-pyridazin-3-ylideneamine $^1$H-NMR (CDCl$_3$) δ 8.35 (d, 1H, J=4 Hz), 7.68 (dd, 1H, J=4, 8.2 Hz), 7.16 (d, 1H, J=8.2 Hz), 6.60 (d, 1H, J=12.75 Hz), 6.52 (d, 1H, J=12.75 Hz), 5.70 (br s, 1H), 5.05 (s, 2H). $^{13}$C-NMR (CDCl$_3$) δ 154.9, 150.7, 149.9, 139.2, 134.8, 132.4, 130.7, 128.1, 124.0, 52.4. Mass spectrum: m/e=255, 257.

EXAMPLE 8

N-(6-Chloro-pydridin-3-ylmethyl)-3H-benzothiazol-2-ylideneamine $^1$H-NMR (CDCl$_3$) δ 8.37 (m, 1H), 7.62 (m, 1H), 7.25 (m, 2H), 7.12 (m, 1H), 6.95 (m, 1H), 6.72 (m, 1H), 5.12 (s, 2H). $^{13}$C-NMR (CDCl$_3$) δ 161.9, 150.7, 148.6, 139.7, 138.0, 130.8, 126.4, 124.2, 122.6, 122.3, 122.0, 109.4, 43.0. Mass spectrum: m/e=276, 278.

EXAMPLE 9

N-Pyridin-3-ylmethyl-3H-[1,3,4]thiadiazol-2-ylideneamine $^1$H-NMR (CDCl$_3$) δ 8.62 (S, 1H), 8.50 (M, 1H), 7.68 (M, 1H),7.55 (S. 1H), 7.22 (M, 1H), 5.09 (D, 2H). $^{13}$C-NMR (CDCl$_3$) δ 161.1, 149.7, 149.2, 135.9, 133.0, 132.0, 123.4, 48.4. Mass spectrum: m/e=193 (P+1).

EXAMPLE 10

N-[1-(6-Chloro-pyridin-3-yl)-ethyl]-3H-thiazol-2-ylideneamine $^1$H-NMR (CDCl$_3$) δ 8.7 (s, 1H), 7.55 (d, 1H, J=8.2 Hz), 7.25 (d, 1H, J=8.2 Hz), 6.41 (d, J=3 Hz), 5.90(d, J=3 Hz), 5.72 (q, 1H), 1.65 (d, 3H).). $^{13}$C-NMR (CDCl$_3$) δ 164.5, 150.8, 148.0, 137.5, 135.4, 124.3, 123.4, 99.9, 50.6, 19.4. Mass spectrum: m/e=239, 241.

EXAMPLE 11

N-[1-(6-Chloro-pyridin-3-yl)-ethyl]-3H-[1,3,4]thiadiazol-2-ylideneamine $^1$H-NMR (CDCl$_3$) δ 8.35 (s, 1H), 7.52 (d, 1H, J=8Hz), 7.51 (s, 1H), 7.25 (d, J=8 Hz), 5.43 (q, 1H), 1.70 (d, 3H). $^{13}$C-NMR (CDCl$_3$) δ 160;9, 150.6, 148.7, 137.6, 135.6, 132.9, 124.0, 52.1, 19.7. Mass spectrum: m/e=240, 242.

EXAMPLE 12

N-[1-(6-Chloro-pyridin-3-ylmethyl)-thiazolidin-2-ylideneamine $^1$H-NMR (CDCl$_3$) δ 8.15 (s, 1H), 7.55 (d, 1H, J=8 Hz), 7.16(d, 1H, J=8 Hz, 6.15 (br s, 1H), 4.45 (s, 2H), 3.40 (t, 2H), 3.05 (t, 2H). $^{13}$C-NMR (CDCl$_3$) δ 164.3, 150.4, 149.0, 138.8, 131.8, 124.2, 51.2,46.0, 26.9. Mass spectrum: m/e= 228, 230.

EXAMPLE 13

N-(Pyridin-3-ylmethyl)-thiazolidin-2-ylideneamine $^1$H-NMR (CDCl$_3$) δ 8.45 (m, 2H), 7.65 (m, 1H), 7.22 (m, 1H), 5.05 (br s, 1H), 4.55 (s, 2H), 3.44 (t, 2H), 3.07 (t, 2H). $^{13}$C-NMR (CDCl$_3$) δ 164.6, 149.3, 148.9, 135.8, 132.7, 123.6, 51.2, 46.8, 26.9. Mass spectrum: m/e=194 (p+1).

EXAMPLE 14

5,7-Dimethyl-N-(pyridin-3-ylmethyl)-3H-[1,8]naphthyridin-2-ylidene

A mixture of 1.27 g (0.01 m) of 3-chloromethylpyridine and 1.43 g (0.083 m) of 7-amino-2,4-dimethyl-1,8-naphthyridine in 15 mL of ethanol was refluxed for 16 hours. The reaction mixture was cooled to room temperature and filtered. The solvent was evaporated and the residue was chromatographed on 150 g silica using 10:1 CHCl$_3$:methanol as the eluant. Appropriate fractions were combined and the solvent evaporated. The residue was recrystallized from isopropyl alcohol to yield 60 mg of the free base form of the title product. M.P. 256–259°. $^1$H-NMR (DMSO-d$_6$) δ 8.6 (m, 1H), 8.5 (m, 2H), 7.6 (d, 1H), 7.4 (s, 1H), 7.35 (m, 1H), 7.29 (d, 1H), 5.95 (s, 2H), 2.63 (s, 3H), 2.53 (s, 3H). Mass spectrum: m/e=265.2 (p+1).

EXAMPLE 15

6-Chloro-N-(pyridin-3-ylmethyl)-2H-pyridazin-3-ylideneamine

This compound was prepared according to the method of Example 14. Mass spectrum: m/e=221/223.

EXAMPLE 16

5-Methyl-N-(pyridin-3-ylmethyl)-3H-[1,3,4]thiadiazol-2-ylideneamine

A. To a solution of 100 mg (0.32 mM) of the hydrochloride salt of title product of Example 6, in 100 mL of methanol, was added 200 mg of 10% Pd/C. This mixture was hydrogenated at 345 kPa (50 psi) for 12 hours. The reaction mixture was filtered and the solvent was removed from the filtrate by evaporation. The residue was dissolved in 25 mL of ethyl acetate and washed with saturated sodium bicarbonate The organic layer was dried (Na$_2$SO$_4$) and the solvent was evaporated to yield 50 mg of the of the title product as an amorphous solid. $^1$H-NMR (CDCl$_3$) δ 8.62 (m, 1H), 8.50 (m, 1H), 7.68 (m, 1H), 7.20 (m, 1H), 5.02 (s, 2H), 2.20 (s, 3H). $^{13}$C-NMR (CDCl$_3$) δ 163.2, 149.5, 149.0, 135.8, 132.3, 123.4, 48.1, 17.0. Mass spectrum: m/e=207 (p+1).

The compound of Example 17 was prepared according to the method of Example 16.

EXAMPLE 17

5,7-Dimethyl-1(6-chloro-pyridin-3-ylmethyl)-1H-[1,8]naphthyridin-2-ylideneamine base: $^1$H-NMR (DMSO-d$_6$) δ 9.5 (br s, 1H), 8.53 (d, 1H), 8.40 (s, 1H), 7.67 (d, 1H), 7.50 (d, 1H), 7.40 (s, 1H), 7.20 (d, 1H), 5.90 (s, 2H), 2.62 (s, 3H), 2.55 (s, 3H). Mass spectrum: m/e=299, 301 (P, P+2).

EXAMPLE 18

3-Pyridin-2-ylmethyl-3H-[1,3,4]thiadiazol-2-ylideneamine hydrochloride

A mixture of 2-chloromethylpyridine (1.75 g, 0.0137 M) and 2-amino-1,3,4-thiadiazole (1.09 g, 0.0108 M) in 20 mL ethyl alcohol was refluxed for 20 hours. The reaction mixture was cooled to room temperature and filtered. The precipitate was washed with ethyl acetate and dried to yield 0.680 g of the title compound. MP=187–189° C. $^1$H-NMR (DMSO-d$_6$) δ 10.6 (br s, 1H), 9.0 (s, 1H), 8.5 (d, 1H), 7.9 (m, 1H), 7.48 (d, 1H), 7.38 (m, 1H), 5.7 (s, 2H). $^{13}$C-NMR (DMSO-d$_6$) δ 167.7, 153.0, 149.3, 145.0, 137.4, 123.4, 122.4, 54.0. Mass spectrum: m/e=193 (p+1).

We claim:

1. A (N-(pyridinylmethyl)-heterocyclic)ylideneamine compound of the formula

I or a pharmaceutically acceptable salt or prodrug thereof, wherein A is —CH(R)— and R is hydrogen or optionally substituted (C$_1$–C$_6$)alkyl wherein the substituents comprise one or more groups individually selected from hydroxy, (C$_1$–C$_6$)alkoxy, oxo, (C$_2$–C$_6$)alkanoyl and NR$^4$R$^5$; and B is a group of the formula

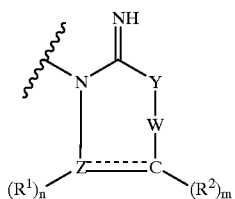

wherein Y-W is $CH_2$, NH; O, S, $CH_2CH_2$, CH=CH, N=CH, NH—$CH_2$, $OCH_2$ or $SCH_2$;

the dotted line represents an optional bond;

Z is C, N, O or S;

m is 1 or 2;

n is 0, 1 or 2 with the proviso that n is 0 when Z is O or S, n is 1 when Z is N and n is 2 when Z is C;

each $R^1$ and $R^2$ is independently selected from hydrogen, optionally substituted ($C_1$–$C_6$)alkyl, optionally substituted ($C_1$–$C_6$)alkoxy and optionally substituted ($C_2$–$C_6$)alkanoyl, wherein the substituents on the alkyl or alkanoyl groups are selected from hydroxy, ($C_1$–$C_6$) alkoxy, oxo, ($C_2$–$C_6$)alkanoyl and $NR^4R^5$, or $R^1$ and $R^2$ together with the carbon atoms to which they are attached form an optionally substituted phenyl ring or six membered heteroaromatic ring containing at least one heteroatom selected from N, S and O and Z is C wherein said substituents are selected from optionally substituted ($C_1$–$C_6$)alkyl or optionally substituted ($C_1$–$C_6$)alkoxy wherein said substituents are selected from ($C_1$–$C_6$)alkyl, optionally substituted ($C_1$–$C_6$) alkoxy and optionally substituted ($C_2$–$C_6$)alkanoyl or $R^1$ and one of $R^2$ together form a bond with the proviso that $R^1$ and $R^2$ cannot form a bond when Z is O or S;

$R^3$ is hydrogen or halo; and $R^4$ and $R^5$ are each independently selected from hydrogen and optionally substituted ($C_1$–$C_6$)alkyl wherein said substituents are selected from ($C_1$–$C_6$)alkyl and halo;

with the provisos that when -B-A is attached to the 3-position of the pyridine ring and R is hydrogen and a) $R^3$ is 6-chloro and
  i) Z is C, the dotted line represents a bond, m and n are both 1, $R^1$ and $R^2$ are both hydrogen, then W-Y is not selected from CH=CH, S, $CH_2$, NH, CH=N, $OCH_2$ or $SCH_2$; or
  ii) Z is nitrogen, the dotted line represents a bond, n is 0 and m is 1 then $R^2$ is not $CF_3$; or
  iii) Z is C, the dotted line represents a single bond, m and n are both 2, and each $R^1$ and $R^2$ is hydrogen, then W-Y is not S; or b) $R^3$ is hydrogen, 6-bromo or 6-fluoro and Z is carbon, the dotted line represents a bond, m and n are both 1, $R^1$ and $R^2$ are both hydrogen, then W-Y is not sulfur.

2. The compound of claim 1 wherein Z is N, m is 1 or 2, W-Y is S or CH=CH, $R^3$ is halo or H, $R^2$ is ($C_1$–$C_6$)alkyl or halo, and the dotted line is a bond.

3. The compound of claim 1 wherein Z is C, R is ($C_1$–$C_6$)alkyl or hydrogen, m is 1, W-Y is S or CH=CH, the dotted line is a bond and, $R^1$ and $R^2$ are each hydrogen or ($C_1$–$C_6$)alkyl, or the portion of B corresponding to

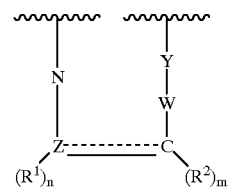

is selected from

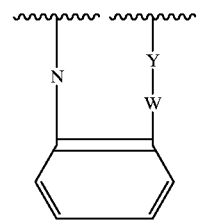

and

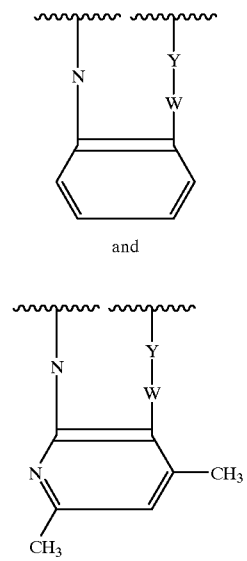

4. The compound according to claim 1 selected from the group consisting of 3-(6-chloro-pyridin-ylmethyl)-3H-[1,3,4]thiadiazol-2-ylideneamine;

5-methyl-3-pyridin-3-ylmethyl-3H-thiazol-2-ylideneamine;

3-(6-chloro-pyridin-3-ylmethyl)-5-methyl-3H-[1,3,4] thiadiozol-2-ylideneamine;

6-chloro-2-(6-chloro-pyridin-3-ylmethyl)-2H-pyridazin-3-ylideneamine;

3-(6chloro-pyridin-3-ylmethyl)-3H-benzothiazol-2-ylideneamine;

3-pyridin-3-ylmethyl-3H-[1,3,4]thiadiazol-2-ylideneamine;

3-[1-(6-chloro-pyridin-3-yl)-ethyl]-3H-thiazol-2-ylideneamine;

3-[1-(6-chloro-pyridin-3-yl)-ethyl]-3H-[1,3,4]thiadiazol-2-ylideneamine;

3-[1-(6-chloro-pyridin-3-ylmethyl)-thiazolidin-2-ylideneamine;

3-pyridin-3-ylmethyl-thiazolidin-2-ylideneamine;

5,7-dimethyl-1-pyridin-3-ylmethyl-3H-[1,8] naphthyridin-2-ylidene;

6-chloro-2-pyridin-3-ylmethyl-2H-pyridazin-3-ylideneamine; and 5-methyl-3-pyridin-3-ylmethyl-3H-[1,3,4]thiadiazol-2-ylideneamine.

5. The compound according to claim 1 or a racemate, stereoisomer or mixture thereof.

6. The compound according to claim 1 comprising at least one radiolabel selected from $^3$H, $^{11}$C and $^{14}$C.

7. The compound according to claim 6 wherein said radiolabel is $^3$H.

8. The compound according to claim 6 wherein said radiolabel is $^{11}$C.

9. The compound according to claim 6 wherein said radiolabel is $^{14}$C.

10. A pharmaceutical composition for treating nicotine addiction or neurological or mental disorders in a mammal comprising an amount of a compound of the formula I, according to claim 1, or a pharmaceutically acceptable salt or prodrug thereof, effective in reducing nicotine addiction and a pharmaceutically acceptable carrier, wherein A is —CH(R)— and R is hydrogen or optionally substituted ($C_1$–$C_6$)alkyl wherein the substituents comprise one or more groups individually selected from hydroxy, ($C_1$–$C_6$)alkoxy, oxo, ($C_2$–$C_6$)alkanoyl and $NR^4R^5$; and B is a group of the formula

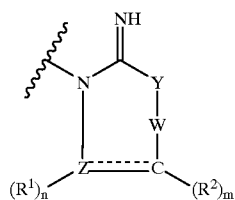

wherein Y-W is $CH_2$, NH, O, S, $CH_2CH_2$, CH=CH, N=CH, NH—$CH_2$, $OCH_2$ or $SCH_2$;

the dotted line represents an optional bond;

Z is C, N, O or S;

m is 1 or 2;

n is 0, 1 or 2 with the proviso that n is 0 when Z is O or S, n is 1 when Z is N and n is 2 when Z is C;

each $R^1$ and $R^2$ is independently selected from hydrogen, optionally substituted ($C_1$–$C_6$)alkyl, optionally substituted ($C_1$–$C_6$)alkoxy and optionally substituted ($C_2$–$C_6$)alkanoyl, wherein the substituents on the alkyl or alkanoyl groups are selected from hydroxy, ($C_1$–$C_6$) alkoxy, oxo, ($C_2$–$C_6$)alkanoyl and $NR^4R^5$, or $R^1$ and $R^2$ together with the carbon atoms to which they are attached form an optionally substituted phenyl ring or six membered heteroaromatic ring containing at least one heteroatom selected from N, S and O and Z is C wherein said substituents are selected from optionally substituted ($C_1$–$C_6$)alkyl or optionally substituted ($C_1$–$C_6$)alkoxy wherein said substituents are selected from ($C_1$–$C_6$)alkyl, optionally substituted ($C_1$–$C_6$) alkoxy and optionally substituted ($C_2$–$C_6$)alkanoyl or $R^1$ and one of $R^2$ together form a bond with the proviso that $R^1$ and $R^2$ cannot form a bond when Z is O or S;

$R^3$ is hydrogen or halo; and $R^4$ and $R_5$ are each independently selected from hydrogen and optionally substituted ($C_1$–$C_6$)alkyl wherein said substituents are selected from ($C_1$–$C_6$)alkyl and halo.

11. The composition of claim 10 wherein the compound of the formula I is selected from selected from the group consisting of 3-(6-chloro-pyridin-3-ylmethyl)-3H-[1,3,4]thiadiazol-2-ylideneamine;

3-pyridin-3-ylmethyl-3H-thiazol-2-ylideneamine;

3-(6-chloro-pyridin-3-ylmethyl)-3H-thiazol-2-ylideneamine;

3-(6-chloro-pyridin-3-ylmethyl)4-methyl-3H-thiazol-2-ylideneamine;

3-(6-chloro-pyridin-3-ylmethyl)-4-methyl-3H-thiazol-2-ylideneamine;

5-methyl-3-pyridin-3-ylmethyl-3H-thiazol-2-ylideneamine;

3-(6-chloro-pyridin-3-ylmethyl)-5-methyl-3H-[1,3,4] thiadiozol-2-ylideneamine;

6-chloro-2-(6-chloro-pyridin-3-ylmethyl)-2H-pyridazin-3-ylideneamine;

3-(6-chloro-pyridin-3-ylmethyl)-3H-benzothiazol-2-ylideneamine;

3-pyridin-3-ylmethyl-3H-[1,3,4]thiadiazol-2-ylideneamine;

3-[1-(6-chloro-pyridin-3-yl)-ethyl]-3H-thiazol-2-ylideneamine;

3-[1-(6-chloro-pyridin-3-yl)-ethyl]-3H-[1,3,4]thiadiazol-2-ylideneamine;

3-[1-(6-chloro-pyridin-3-ylmethyl)-thiazolidin-2-ylideneamine;

3-pyridin-3-ylmethyl-thiazolidin-2-ylideneamine;

5,7-dimethyl-1-pyridin-3-ylmethyl-3H-[1,8] naphthyridin-2-ylidene;

6-chloro-2-pyridin-3-ylmethyl-2H-pyridazin-3-ylideneamine; and 5-methyl-3-pyridin-3-ylmethyl-3H-[1,3,4]thiadiazol-2-ylideneamine.

12. A method for reducing nicotine addiction in a mammal, comprising administering to said mammal an amount of a compound of the formula I according to claim 1, or a pharmaceutically acceptable salt or prodrug thereof, effective in reducing nicotine addiction wherein A is —CH (R)— and R is hydrogen or optionally substituted ($C_1$–$C_6$) alkyl wherein the substituents comprise one or more groups individually selected from hydroxy, ($C_1$–$C_6$)alkoxy, oxo, ($C_2$–$C_6$)alkanoyl and $NR^4R^5$; and B is a group of the formula

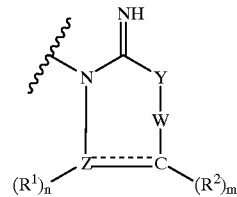

wherein Y-W is $CH_2$, NH, O, S, $CH_2CH_2$, CH=CH, N=CH, NH—$CH_2$, $OCH_2$ or $SCH_2$;

the dotted line represents an optional bond;

Z is C, N, O or S;

m is 1 or 2;

n is 0, 1 or 2 with the proviso that n is 0 when Z is O or S, n is 1 when Z is N and n is 2 when Z is C;

each $R^1$ and $R^2$ is independently selected from hydrogen, optionally substituted ($C_1$–$C_6$)alkyl, optionally substituted ($C_1$–$C_6$)alkoxy and optionally substituted ($C_2$–$C_6$)alkanoyl, wherein the substituents on the alkyl or alkanoyl groups are selected from hydroxy, ($C_1$–$C_6$) alkoxy, oxo, ($C_2$–$C_6$)alkanoyl and $NR^4R^5$, or $R^1$ and $R^2$ together with the carbon atoms to which they are attached form an optionally substituted phenyl ring or six membered heteroaromatic ring containing at least one heteroatom selected from N, S and O and Z is C wherein said substituents are selected from optionally substituted (C$_1$–C$_6$)alkyl or optionally substituted (C$_1$–C$_6$)alkoxy wherein said substituents are selected from (C$_1$–C$_6$) optionally substituted (C$_1$–C$_6$)alkoxy and optionally substituted (C$_2$–C$_6$)alkanoyl or R$^1$ and one of R$^2$ together form a bond with the proviso that R$^1$ and R$^2$ cannot form a bond when Z is O or S;

R$^3$ is hydrogen or halo; and

R$^4$ and R$^5$ are each independently selected from hydrogen and optionally substituted (C$_1$–C$_6$)alkyl wherein said substituents are selected from (C$_1$–C$_6$)alkyl and halo.

13. The method of claim 12 wherein the compound of the formula I is selected from selected from the group consisting of 3-(6-chloro-pyridin-3-ylmethyl)-3H-[1,3,4]thiadiazol-2-ylideneamine;

3-pyridin-3-ylmethyl-3H-thiazol-2-ylideneamine;

3-(6-chloro-pyridin-3-ylmethyl)-3H-thiazol-2-ylideneamine;

3-(6-chloro-pyridin-3-ylmethyl)-4-methyl-3H-thiazol-2-ylideneamine;

3-(6-chloro-pyridin-3-ylmethyl)-4-methyl-3H-thiazol-2-ylideneamine;

5-methyl-3-pyridin-3-ylmethyl-3H-thiazol-2-ylideneamine;

3-(6-chloro-pyridin-3-ylmethyl)-5-methyl-3H-[1,3,4]thiadiozol-2-ylideneamine;

6chloro-2-(6-chloro-pyridin-3-ylmethyl)-2H-pyridazin-3-ylideneamine;

3-(6-chloro-pyridin-3-ylmethyl)-3H-benzothiazol-2-ylideneamine;

3-pyridin-3-ylmethyl-3H-[1,3,4]thiadiazol-2-ylideneamine;

3-[1-(6chloro-pyridin-3-yl)-ethyl]-3H-thiazol-2-ylideneamine;

3-[1-(6-chloro-pyridin-3-yl)-ethyl]-3H-[1,3,4]thiadiazol-2-ylideneamine;

3-[1-(6-chloro-pyridin-3-ylmethyl)-thiazolidin-2-ylideneamine;

3-pyridin-3-ylmethyl-thiazolidin-2-ylideneamine;

5,7-dimethyl-1-pyridin-3-ylmethyl-3H-[1,8]naphthyridin-2-ylidene;

6-chloro-2-pyridin-3-ylmethyl-2H-pyridazin-3-ylideneamine; and 5-methyl-3-pyridin-3-ylmethyl-3H-[1,3,4]thiadiazol-2-ylideneamine.

14. The compound according to claim 1 wherein said pharmaceutically acceptable acid addition salt is a salt of an acid selected from the group comprising hydrochloric acid, p-toluenesulfonic acid, fumaric acid, citric acid, succinic acid, salicyclic acid, oxalic acid, hydrobromic acid, phosphoric acid, methanesulfonic acid, tartaric acid, di-p-toluoyl tartaric acid, and mandelic acid.

15. A method for treating nicotine addiction or neurological or mental disorders in a mammal which comprises administering to said mammal an amount of a compound of the formula I according to claim 1 effective in treating nicotine addiction or neurological or mental disorders wherein A is —CH(R)— and R Is hydrogen or optionally substituted (C$_1$–C$_6$)alkyl wherein the substituents comprise one or more groups individually selected from hydroxy, (C$_1$–C$_6$)alkoxy, oxo, (C$_2$–C$_6$,)alkanoyl and NR$^4$R$^5$; and B is a group of the formula

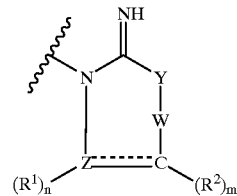

wherein Y-W is CH$_2$, NH, O, S, CH$_2$CH$_2$, CH=CH, N=CH, NH—CH$_2$, OCH$_2$or SCH$_2$;

the dotted line represents an optional bond;

Z is C, N, O or S;

m is 1 or 2;

n is 0, 1 or 2 with the proviso that n is 0 when Z is O or S, n is 1 when Z is N and n is 2 when Z is C;

each R$^1$ and R$^2$ is independently selected from hydrogen, optionally substituted (C$_1$–C$_6$)alkyl, optionally substituted (C$_1$–C$_6$)alkoxy and optionally substituted (C$_2$–C$_6$)alkanoyl, wherein the substituents on the alkyl or alkanoyl groups are selected from hydroxy, (C$_1$–C$_6$) alkoxy, oxo, (C$_2$–C$_6$)alkanoyl and NR$^4$R$^5$, or R$^1$ and R$^2$ together with the carbon atoms to which they are attached form an optionally substituted phenyl ring or six membered heteroaromatic ring containing at least one heteroatom selected from N, S and O and Z is C wherein said substituents are selected from optionally substituted (C$_1$–C$_6$)alkyl or optionally substituted (C$_1$–C$_6$)alkoxy wherein said substituents are selected from (C$_1$–C$_6$)alkyl, optionally substituted (C$_1$–C$_6$) alkoxy and optionally substituted (C$_2$–C$_6$)alkanoyl or R$^1$ and one of R$^2$ together form a bond with the proviso that R$^1$ and R$^2$ cannot form a bond when Z is O or S;

R$^3$ is hydrogen or halo; and

R$^4$ and R$^5$ are each independently selected from hydrogen and optionally substituted (C$_1$–C$_6$)alkyl wherein said substituent are selected from (C$_1$–C$_6$)alkyl and halo.

16. The method of claim 15 wherein the compound of the formula I is selected from the group consisting of 3-(6-chloro-pyridin-3-ylmethyl)-3H-[1,3,4]thiadiazol-2-ylideneamine;

3-pyridin-3-ylmethyl-3H-thiazol-2-ylideneamine;

3-(6-chloro-pyridin-3-ylmethyl)-3H-thiazol-2-ylideneamine;

3-(6-chloro-pyridin-3-ylmethyl)-4-methyl-3H-thiazol-2-ylideneamine;

3-(6-chloro-pyridin-3-ylmethyl)-4-methyl-3H-thiazol-2-ylideneamine;

5-methyl-3-pyridin-3-ylmethyl-3H-thiazol-2-ylideneamine;

3-(6-chloro-pyridin-3-ylmethyl)-5-methyl-3H-[1,3,4]thiadiozol-2-ylideneamine;

6-chloro-2-(6-chloro-pyridin-3-ylmethyl)-2H-pyridazin-3-ylideneamine;

3-(6-chloro-pyridin-3-ylmethyl)-3H-benzothiazol-2-ylideneamine;

3-pyridin-3-ylmethyl-3H-[1,3,4]thiadiazol-2-ylideneamine;

3-[1-(6-chloro-pyridin-3-yl)-ethyl]-3H-thiazol-2-ylideneamine;

3-[1-(6-chloro-pyridin-3-yl)-ethyl]-3H-[1,3,4]thiadiazol-2-ylideneamine;

3-[1-(6-chloro-pyridin-3-ylmethyl)-thiazolidin-2-ylideneamine;

3-pyridin-3-ylmethyl-thiazolidin-2-ylideneamine;

5,7-dimethyl-1-pyridin-3-ylmethyl-3H-[1,8]naphthyridin-2-ylidene;

6-chloro-2-pyridin-3-ylmethyl-2H-pyridazin-3-ylideneamine; and 5-methyl-3-pyridin-3-ylmethyl-3H-[1,3,4]thiadiazol-2-ylideneamine.

* * * * *